US010439385B1

United States Patent
Wu et al.

(10) Patent No.: US 10,439,385 B1
(45) Date of Patent: Oct. 8, 2019

(54) BIOMEDICAL STIMULATION PROTECTION DEVICE

(71) Applicant: NATIONAL CHIAO TUNG UNIVERSITY, Hsinchu (TW)

(72) Inventors: Chung-Yu Wu, Hsinchu (TW); Chi-Wei Huang, Hsinchu (TW); Cheng-Hsiang Cheng, New Taipei (TW)

(73) Assignee: National Chiao Tung University, Hsinchu (TW)

( * ) Notice: Subject to any disclaimer, the term of this patent is extended or adjusted under 35 U.S.C. 154(b) by 0 days.

(21) Appl. No.: 16/367,670

(22) Filed: Mar. 28, 2019

(30) Foreign Application Priority Data

Oct. 9, 2018 (TW) .............................. 107135480 A (51) Int. Cl.
| | | |
|---|---|---|
| H02M 1/00 | (2006.01) | |
| H02H 1/06 | (2006.01) | |
| A61N 1/378 | (2006.01) | |
| H02H 3/20 | (2006.01) | |
| H02M 1/32 | (2007.01) | |

(52) U.S. Cl.
CPC .............. H02H 1/06 (2013.01); A61N 1/378 (2013.01); H02H 3/20 (2013.01); H02M 1/32 (2013.01)

(58) Field of Classification Search
CPC .............. H02H 1/06; H02H 3/20; H02M 1/32
See application file for complete search history.

(56) References Cited

U.S. PATENT DOCUMENTS 9,960,594 B1 * 5/2018 Lin .................... H02H 9/044
2012/0170165 A1 7/2012 Jung et al.

FOREIGN PATENT DOCUMENTS

| TW | 201442760 A | 11/2014 |
|---|---|---|
| TW | I492738 B | 7/2015 |

OTHER PUBLICATIONS

H. Kijima. "Overvoltage Protective Device and Method of Overvoltage Protection." Proc. 8th WSEAS Int. Conf. on Electronics, Hardware, Wireless and Optical Communications (Feb. 2009), pp. 155-160.

(Continued)

*Primary Examiner* — Adolf D Berhane
*Assistant Examiner* — Afework S Demisse
(74) *Attorney, Agent, or Firm* — Rosenberg, Klein & Lee (57) ABSTRACT

A biomedical stimulation protection device includes a current source, a first upper P-channel metal oxide semiconductor field effect transistor (PMOSFET), a first adaptive bias circuit, and six first stimulating metal oxide semiconductor field effect transistors (MOSFETs). The first adaptive bias circuit receives a power voltage (VDD), a double power voltage (2VDD), and a triple power voltage (3VDD). The first upper MOSFET and the first stimulating MOSFETs are electrically cascoded with each other. The first adaptive bias circuit turns on at least one of the first stimulating MOSFETs according to VDD, 2VDD, and 3VDD, so as to stimulate a physiological tissue and control a voltage difference between two terminals of each of the first upper MOSFET and the first stimulating MOSFETs to be lower than or equal to VDD.

12 Claims, 5 Drawing Sheets

(56) References Cited

OTHER PUBLICATIONS

C.-C. Chen & K.-T. Tang. "A 12V-500μA Neuron Stimulator with Current Calibration Mechanism in 0.18μm Standard CMOS Process." Proc. IEEE Biomed. Circuits Syst. Conf. (Nov. 2011), pp. 57-60. doi: 10.1109/BioCAS.2011.6107726.

B. Serneels, et al. "A 1.5W 10V-Output Class-D Amplifier Using a Boosted Supply from a Single 3.3V Input in Standard 1.8V/3.3V 0.18μm CMOS." Digest of Technical Papers for 2012 IEEE Intl. Solid-State Circuits Conf. (Feb 2012), pp. 94-96. doi: 10.1109/ISSCC.2012.6176890.

* cited by examiner

BIOMEDICAL STIMULATION PROTECTION DEVICE

This application claims priority to Taiwan Patent Application No. 107135480, filed on Oct. 9, 2018, the content of which is incorporated by reference in its entirety.

BACKGROUND OF THE INVENTION

1. Field of the Invention

The present invention relates to a stimulation protection device, and more particular to a biomedical stimulation protection device which is able to effectively prevent circuit thereof from being damaged by high voltage.

2. Description of the Related Art

In recent years, the MEMS technology is fully developed and the microsurgery technology is improved, so many medical instruments for detection and control can be miniaturized for implantation into the human body, to compensate the functions of human organs and detect various physiological parameters inside the human body. The implantable biomedical device does not need to pass through skin or gastrointestinal digestive system, and various interference factors are greatly reduced, so the implantable biomedical device can better match with the human body and have advantages of convenient use and comfort. Especially for organs and tissues, the implantable biomedical device is greatly helpful for immediate regulation and for repairing body functions and monitoring the condition. By using the implantable biomedical device, it is possible to directly detect various physiological parameters that are difficult to detect ex vitro, and further continuously and immediately monitor the physiological parameters. As a result, the doctor can provide immediate and efficient healthcare services with assistance of the long-term and continuous physiological health monitoring data, and the remote medical and nursing system.

Generally, an implantable electrical stimulation biomedical treatment system includes an amplifier for measuring physiological signals and capturing analog signals, and a stimulator for generating electrical stimulation. For example, Taiwan Patent No. TWI492738 discloses an implantable closed-loop micro-stimulation device comprising a wireless receiver, a wireless energy conversion and storage interface, a demodulation circuit, a main controller, a front-end sensor and a stimulation generator. The wireless energy conversion and storage interface receives AC signal from the wireless receiver and converts the AC signal into DC power for battery charging and providing a stable operation voltage. The demodulation circuit receives a wireless control signal through the wireless receiver, and demodulates the wireless control signal into a control data and a control clock which are outputted to the main controller. The main controller performs a detection mechanism to determine accuracy of the control data. If the control data is accurate, the main controller outputs the stimulation parameters to the front-end sensor and the stimulation generator according to the control data and the control clock. The front-end sensor receives the physiological signal transmitted from the stimulated tissue, and converts the physiological signal into a digital code for recording. The digital signal processor can analyze the digitized physiological signal and determines, according to the parameters, whether to control the stimulation generator to generate and apply a stimulation pulse signal to the stimulated for treatment. As the integrated circuit process evolves, the power supply voltage required by the integrate circuit gradually decreases, but the withstand voltages of devices of the integrate circuit also decrease. In the biomedical treatment system, high voltage stimulation is often required to achieve an effective clinical treatment effect, but the high voltage stimulation possibly cause the voltage, which is applied to the gate oxide layer of the semiconductor device in the stimulation and signal detection circuit, to exceed the withstand voltage and break the semiconductor device. Conventional techniques use high-voltage processes to produce amplifiers and other circuits for physiological signal acquisition, to solve the overvoltage problem of gate oxide layer of the complementary metal-oxide-semiconductor (CMOS) transistors during stimulation; however, according to the conventional techniques, the process integration of the implantable electrical stimulation biomedical treatment system with the circuit modules of other system on chips is also reduced.

Therefore, the present invention provides a biomedical stimulation protection device to solve the conventional problems.

SUMMARY OF THE INVENTION

An objective of the present invention is to provide a biomedical stimulation protection device. In the biomedical stimulation protection device, an adaptive bias circuit is used to detect an output voltage, to generate an appropriate bias voltage, and the bias voltage is provided to metal-oxide-semiconductor field-effect transistors (abbreviated as MOSFETs hereafter) of a stimulation circuit, so that a voltage difference at any two terminals of each of the MOSFETs can be lower than or equal to a withstand voltage defined in a low-voltage manufacturing process, thereby effectively preventing the MOSFETs and the adaptive bias circuit of the stimulation circuit from being damaged by high voltage.

In order to achieve above-mentioned objective, the present invention provides a biomedical stimulation protection device which can operate in a stimulation mode or a sampling mode. The biomedical stimulation protection device comprises a current source, a first upper p-channel metal-oxide-semiconductor field-effect transistor (abbreviated as PMOSFET hereafter), a first adaptive bias circuit, six first stimulating MOSFETs, and a first lower n-channel metal-oxide-semiconductor field-effect transistor (abbreviated as NMOSFET hereafter). The current source is configured to receive a quadruple power voltage (abbreviated as 4VDD hereafter) in the stimulation mode, to generate a stimulation current. The first upper PMOSFET is electrically connected to the current source, and in the stimulation mode, the first upper PMOSFET receives a triple power voltage (abbreviated as 3VDD hereafter) and is turned on, and the stimulation current flows through the first upper PMOSFET. The first adaptive bias circuit is configured to receive a power voltage (abbreviated as VDD hereafter), a double power voltage (abbreviated as 2VDD hereafter) and 3VDD in the stimulation mode. The six first stimulating MOSFETs are electrically cascoded with each other and electrically cascoded the first upper PMOSFET, and electrically connected to the first adaptive bias circuit. A first central node among the six first stimulating MOSFETs comprises a first output terminal electrically connected to a physiological tissue. In the stimulation mode, according to VDD, 2VDD and 3VDD, the first adaptive bias circuit turns on at least one of the six first stimulating MOSFETs disposed between the first central node and the first upper PMOSFET, to transmit the stimulation current to the physiological tissue and form a first output voltage at the first output terminal. The first lower NMOSFET is electrically connected to ground, and the six first stimulating MOSFETs are electrically cascoded between the first upper PMOSFET and the first lower NMOSFET. In the stimulation mode, the first lower NMOSFET receives zero voltage and is turned off, to block the stimulation current from flowing to ground, and VDD is 6 times of a threshold voltage of the first lower NMOSFET, and the first adaptive bias circuit can control a voltage difference at two terminals of the first lower NMOSFET to be lower than or equal to VDD according to VDD, 2VDD, 3VDD and the first output voltage.

In an embodiment, the biomedical stimulation protection device can comprise a first detecting MOSFET and a second detecting MOSFET. For example, the first detecting MOSFET can be a PMOSFET, and the second detecting MOSFET can be a NMOSFET. The first detecting MOSFET is electrically connected to the first adaptive bias circuit and the first stimulating MOSFETs. In the stimulation mode, the first detecting MOSFET is turned off, and in the sampling mode, the first detecting MOSFET is turned on and receives an external voltage, and the external voltage is equal to VDD. The second detecting MOSFET is electrically connected to the six first stimulating MOSFETs and a signal detector. In the stimulation mode, the second detecting MOSFET is turned off, and in the sampling mode, the second detecting MOSFET is turned on, and the current source receives zero voltage and stops generating the stimulation current, and the first upper PMOSFET receives zero voltage and is turned off, the first adaptive bias circuit receives zero voltage, the first lower NMOSFET receives zero voltage and is turned off, the first detecting MOSFET applies the external voltage to drive the first adaptive bias circuit to turn on at least one of the six first stimulating MOSFETs disposed between the first central node and the first lower NMOSFET, so as to use the at least one of the six first stimulating MOSFETs and the second detecting MOSFET disposed between the first central node and the first lower NMOSFET to transmit a first physiological current from the physiological tissue to the signal detector.

In an embodiment, the biomedical stimulation protection device can comprise a second upper PMOSFET, a second adaptive bias circuit, a second lower NMOSFET and six second stimulating MOSFETs.

The second upper PMOSFET is electrically connected to the current source. In the stimulation mode, the second upper PMOSFET receives 4VDD and is turned off, so as to block the stimulation current from flowing the second upper PMOSFET. The second adaptive bias circuit is configured to receive VDD, 2VDD and 3VDD in the stimulation mode. The second lower NMOSFET is electrically connected to ground, and the second lower NMOSFET receives VDD and is turned on in the stimulation mode. The six second stimulating MOSFETs are electrically cascoded with each other and electrically cascoded between the second upper PMOSFET and the second lower NMOSFET, and electrically connected to the second adaptive bias circuit. A second central node among the six second stimulating MOSFETs comprises a second output terminal electrically connected to the physiological tissue. In the stimulation mode, the second adaptive bias circuit turns on at least one of the six second stimulating MOSFETs disposed between the second central node and the second lower NMOSFET according to VDD, 2VDD and 3VDD, so as to transmit the stimulation current from the physiological tissue to ground through the second lower NMOSFET, and form a second output voltage at the second output terminal. For example, VDD is 6 times of a threshold voltage of each of the second upper PMOSFET, the six second stimulating MOSFETs and the second lower NMOSFET. According to VDD, 2VDD, 3VDD and the second output voltage, the second adaptive bias circuit controls a voltage difference at two terminals of each of the second upper PMOSFET, the six second stimulating MOSFETs and the second lower NMOSFET to be lower than or equal to VDD.

In an embodiment, the biomedical stimulation protection device can comprise a third detecting MOSFET and a fourth detecting MOSFET. For example, the third detecting MOSFET can be a PMOSFET and a fourth detecting MOSFET can be a NMOSFET. The third detecting MOSFET is electrically connected to the second adaptive bias circuit and the six second stimulating MOSFETs. The third detecting MOSFET is turned off in the stimulation mode, and the third detecting MOSFET is turned on and receives the external voltage in the sampling mode. The fourth detecting MOSFET is electrically connected to the six second stimulating MOSFETs and the signal detector. In the stimulation mode, the fourth detecting MOSFET is turned off, and in the sampling mode, the fourth detecting MOSFET is turned on, and the current source receives zero voltage and stops generating the stimulation current, the second upper PMOSFET receives 4VDD and is turned off, the second adaptive bias circuit receives zero voltage, the second lower NMOSFET receives zero voltage and is turned off, the third detecting MOSFET applies the external voltage to drive the second adaptive bias circuit to turn on at least one of the six second stimulating MOSFETs disposed between the second central node and the second lower NMOSFET, so as to use the fourth detecting MOSFET and the at least one of the second stimulating MOSFETs disposed between the second central node and the second lower NMOSFET to transmit a second physiological current from the physiological tissue to the signal detector.

In an embodiment, a gate of the first upper PMOSFET receives 3VDD or zero voltage, a source of the first upper PMOSFET is electrically connected to the current source, and the six first stimulating MOSFETs can comprise a first PMOSFET, a second PMOSFET, a third PMOSFET, a first NMOSFET, a second NMOSFET, and a third NMOSFET. The first PMOSFET comprises a source electrically connected to a drain of the first upper PMOSFET, and a gate receiving 3VDD or zero voltage. The second PMOSFET comprises a source electrically connected to a drain of the first PMOSFET, and a gate electrically connected to the first adaptive bias circuit. The third PMOSFET comprises a source electrically connected to a drain of the second PMOSFET, a gate electrically connected to the first adaptive bias circuit, and a drain electrically connected to the first central node. The first NMOSFET comprises a drain electrically connected to the first central node, and a gate electrically connected to the gate of the third PMOSFET and the first adaptive bias circuit. The second NMOSFET comprises a drain electrically connected to a source of the first NMOSFET, and a gate electrically connected to the first adaptive bias circuit. The third NMOSFET comprises a drain electrically connected to a source of the second NMOSFET, a gate receiving VDD or zero voltage, and a source electrically connected to a drain of the first lower NMOSFET and the second detecting MOSFET. The gate of the third NMOSFET is electrically connected to the first detecting MOSFET and the first adaptive bias circuit. The first lower NMOSFET comprises a gate receiving zero voltage and a source electrically connected to ground. In the stimulation mode, the first adaptive bias circuit turns on the first PMOSFET, the second PMOSFET and the third PMOSFET according to VDD, 2VDD and 3VDD. For example, VDD can be 6 times of a threshold voltage of each of the first PMOSFET, the second PMOSFET, the third PMOSFET, the first NMOSFET, the second NMOSFET and the third NMOSFET. According to VDD, 2VDD, 3VDD and the first output voltage, the first adaptive bias circuit controls a voltage difference at two terminals of each of the first PMOSFET, the second PMOSFET, the third PMOSFET, the first NMOSFET, the second NMOSFET and the third NMOSFET to be lower than or equal to VDD. In in the sampling mode, the first detecting MOSFET applies the external voltage to drive the first adaptive bias circuit to turn on the first NMOSFET, the second NMOSFET and the third NMOSFET, so as to use the first NMOSFET, the second NMOSFET and the third NMOSFET to transmit the first physiological current to the signal detector.

In an embodiment, the first adaptive bias circuit can comprise a fourth PMOSFET, a fourth NMOSFET, a fifth NMOSFET, a sixth NMOSFET, a fifth PMOSFET and a sixth PMOSFET. The fourth PMOSFET comprises a drain receiving 2VDD or zero voltage. The fourth NMOSFET comprises a drain receiving 2VDD or zero voltage, and a gate electrically connected to a gate of the fourth PMOSFET. The fifth NMOSFET comprises a drain receiving 3VDD or zero voltage, and the drain and the gate of the fifth NMOSFET are electrically connected to the gate and the drain of the first PMOSFET, respectively, and a source of the fifth NMOSFET is electrically connected to the source of the fourth PMOSFET and the gate of the second PMOSFET. The sixth NMOSFET comprises a drain electrically connected to the source of the fifth NMOSFET, a gate electrically connected to the drain of the second PMOSFET, and a source electrically connected to the gates of the fourth PMOSFET, the third PMOSFET and the first NMOSFET. The fifth PMOSFET comprises a source electrically connected to the source of the sixth NMOSFET, a gate electrically connected to the source of the first NMOSFET, and a drain electrically connected to the source of the fourth NMOSFET and the gate of the second NMOSFET, and a base electrically connected to the source of the fifth PMOSFET. The fifth PMOSFET comprises a first parasitic body-drain diode. The sixth PMOSFET comprises a source electrically connected to the drain of the fifth PMOSFET, a gate electrically connected to the source of the second NMOSFET, a drain electrically connected to the first detecting MOSFET and the gate of the third NMOSFET, and a base electrically connected to the source of the sixth PMOSFET. The sixth PMOSFET comprises a second parasitic body-drain diode, and VDD can be four to five times of a forward-biased voltage of each of the first parasitic body-drain diode and the second parasitic body-drain diode. The drain of the sixth PMOSFET receives VDD or zero voltage. In the stimulation mode, the fourth PMOSFET, the fourth NMOSFET, the fifth NMOSFET, the sixth NMOSFET, the fifth PMOSFET and the sixth PMOSFET turn on the first PMOSFET, the second PMOSFET and the third PMOSFET according to VDD, 2VDD and 3VDD, and VDD can be 6 times of a threshold voltage of each of the fourth PMOSFET, the fourth NMOSFET, the fifth NMOSFET, the sixth NMOSFET, the fifth PMOSFET and the sixth PMOSFET. VDD, 2VDD, 3VDD and the first output voltage are applied to the first PMOSFET, the second PMOSFET, the third PMOSFET, the first NMOSFET, the second NMOSFET and the third NMOSFET, to control a voltage difference at two terminals of each of the fourth PMOSFET, the fourth NMOSFET, the fifth NMOSFET, the sixth NMOSFET, the fifth PMOSFET and the sixth PMOSFET to be lower than or equal to VDD. In the sampling mode, the first detecting MOSFET applies the external voltage to drive the fifth PMOSFET and the sixth PMOSFET to turn on the first NMOSFET, the second NMOSFET and the third NMOSFET.

In an embodiment, the gate of the second upper PMOSFET receives 4VDD or zero voltage, the source of the second upper PMOSFET is electrically connected to the current source, and the six second stimulating MOSFETs comprise a seventh PMOSFET, an eighth PMOSFET, a ninth PMOSFET, a seventh NMOSFET, an eighth NMOSFET, a ninth NMOSFET. The seventh PMOSFET comprises a source electrically connected to a drain of the second upper PMOSFET, and a gate receiving 3VDD or zero voltage. The eighth PMOSFET comprises a source electrically connected to a drain of the seventh PMOSFET, and a gate electrically connected to the second adaptive bias circuit. The ninth PMOSFET comprises a source electrically connected to a drain of the eighth PMOSFET, a gate electrically connected to the second adaptive bias circuit, and a drain electrically connected to the second central node. The seventh NMOSFET comprises a drain electrically connected to the second central node, and a gate electrically connected to a gate of the ninth PMOSFET and the second adaptive bias circuit. The eighth NMOSFET comprises a drain electrically connected to a source of the seventh NMOSFET, and a gate electrically connected to the second adaptive bias circuit. The ninth NMOSFET comprises a drain electrically connected to a source of the eighth NMOSFET, a gate receiving VDD or zero voltage, a source electrically connected to the drain of the second lower NMOSFET and the fourth detecting MOSFET. The gate of the ninth NMOSFET is electrically connected to the third detecting MOSFET and the second adaptive bias circuit, the gate of the second lower NMOSFET receives VDD, a source of the second lower NMOSFET is electrically connected to ground. In the stimulation mode, the second adaptive bias circuit turns on the seventh NMOSFET, the eighth NMOSFET and the ninth NMOSFET according to VDD, 2VDD and 3VDD, and VDD is 6 times of a threshold voltage of each of the seventh PMOSFET, the eighth PMOSFET, the ninth PMOSFET, the seventh NMOSFET, the eighth NMOSFET and the ninth NMOSFET. According to VDD, 2VDD, 3VDD and the second output voltage, the second adaptive bias circuit controls a voltage difference at two terminals of each of the seventh PMOSFET, the eighth PMOSFET, the ninth PMOSFET, the seventh NMOSFET, the eighth NMOSFET and the ninth NMOSFET to be lower than or equal to VDD. In the sampling mode, the third detecting MOSFET applies the external voltage to drive the second adaptive bias circuit to turn on the seventh NMOSFET, the eighth NMOSFET and the ninth NMOSFET, so as to use the seventh NMOSFET, the eighth NMOSFET and the ninth NMOSFET to transmit the second physiological current to the signal detector.

In an embodiment, the second adaptive bias circuit comprises a tenth PMOSFET, a tenth NMOSFET, an eleventh NMOSFET, a twelfth NMOSFET, an eleventh PMOSFET, and a twelfth PMOSFET. The tenth PMOSFET comprises a drain receiving 2VDD or zero voltage. The tenth NMOSFET comprises a drain receiving 2VDD or zero voltage, and a gate electrically connected to a gate of the tenth PMOSFET. The eleventh NMOSFET comprises a drain receiving 3VDD or zero voltage, and a drain and a gate of the eleventh NMOSFET are electrically connected to the gate and the drain of the seventh PMOSFET, respectively, and a source of the eleventh NMOSFET is electrically connected to a source of the tenth PMOSFET and the gate of the eighth PMOSFET. The twelfth NMOSFET comprises a drain electrically connected to the source of the eleventh NMOSFET, a gate electrically connected to the drain of the eighth PMOSFET, and a source electrically connected to the gates of the tenth PMOSFET, the ninth PMOSFET and the seventh NMOSFET. The eleventh PMOSFET comprises a source electrically connected to the source of the twelfth NMOSFET, a gate electrically connected to the source of the seventh NMOSFET, a drain electrically connected to a source of the tenth NMOSFET and the gate of the eighth NMOSFET, and a base electrically connected to the source of the eleventh PMOSFET. The eleventh PMOSFET comprise a third parasitic body-drain diode. The twelfth PMOSFET comprises a source electrically connected to the drain of the eleventh PMOSFET, a gate electrically connected to the source of the eighth NMOSFET, a drain electrically connected the third detecting MOSFET and the gate of the ninth NMOSFET, and a base electrically connected to the source of the twelfth PMOSFET. The twelfth PMOSFET comprises a fourth parasitic body-drain diode. For example, VDD can be four to five times of a forward-biased voltage of each of the third parasitic body-drain diode and the fourth parasitic body-drain diode. The drain of the twelfth PMOSFET receives VDD or zero voltage. In the stimulation mode, the tenth PMOSFET, the tenth NMOSFET, the eleventh NMOSFET, the twelfth NMOSFET, the eleventh PMOSFET and the twelfth PMOSFET turn on the seventh NMOSFET, the eighth NMOSFET and the ninth NMOSFET according to VDD, 2VDD and 3VDD, wherein VDD is six times of a threshold voltage of each of the tenth PMOSFET, the tenth NMOSFET, the eleventh NMOSFET, the twelfth NMOSFET, the eleventh PMOSFET and the twelfth PMOSFET. VDD, 2VDD, 3VDD and the second output voltage are applied to the seventh PMOSFET, the eighth PMOSFET, the ninth PMOSFET, the seventh NMOSFET, the eighth NMOSFET and the ninth NMOSFET to control a voltage difference at two terminals of each of the tenth PMOSFET, the tenth NMOSFET, the eleventh NMOSFET, the twelfth NMOSFET, the eleventh PMOSFET and the twelfth PMOSFET to be lower than or equal to VDD. In the sampling mode, the third detecting MOSFET applies the external voltage to drive the eleventh PMOSFET and the twelfth PMOSFET to turn on the seventh NMOSFET, the eighth NMOSFET and the ninth NMOSFET.

BRIEF DESCRIPTION OF THE DRAWINGS

The structure, operating principle and effects of the present invention will be described in detail by way of various embodiments which are illustrated in the accompanying drawings.

DETAILED DESCRIPTION OF THE PREFERRED EMBODIMENTS

The following embodiments of the present invention are herein described in detail with reference to the accompanying drawings. These drawings show specific examples of the embodiments of the present invention. It is to be understood that these embodiments are exemplary implementations and are not to be construed as limiting the scope of the present invention in any way. Further modifications to the disclosed embodiments, as well as other embodiments, are also included within the scope of the appended claims. These embodiments are provided so that this disclosure is thorough and complete, and fully conveys the inventive concept to those skilled in the art. Regarding the drawings, the relative proportions and ratios of elements in the drawings may be exaggerated or diminished in size for the sake of clarity and convenience. Such arbitrary proportions are only illustrative and not limiting in any way. The same reference numbers are used in the drawings and description to refer to the same or like parts.

It is to be understood that although the terms 'first', 'second', 'third', and so on, may be used herein to describe various elements, these elements should not be limited by these terms. These terms are used only for the purpose of distinguishing one component from another component. Thus, a first element discussed herein could be termed a second element without altering the description of the present disclosure. As used herein, the term "or" includes any and all combinations of one or more of the associated listed items.

It will be understood that when an element or layer is referred to as being "on," "connected to" or "coupled to" another element or layer, it can be directly on, connected or coupled to the other element or layer, or intervening elements or layers may be present. In contrast, when an element is referred to as being "directly on," "directly connected to" or "directly coupled to" another element or layer, there are no intervening elements or layers present.

In addition, unless explicitly described to the contrary, the word "comprise" and variations such as "comprises" or "comprising", will be understood to imply the inclusion of stated elements but not the exclusion of any other elements.

Figure 1:
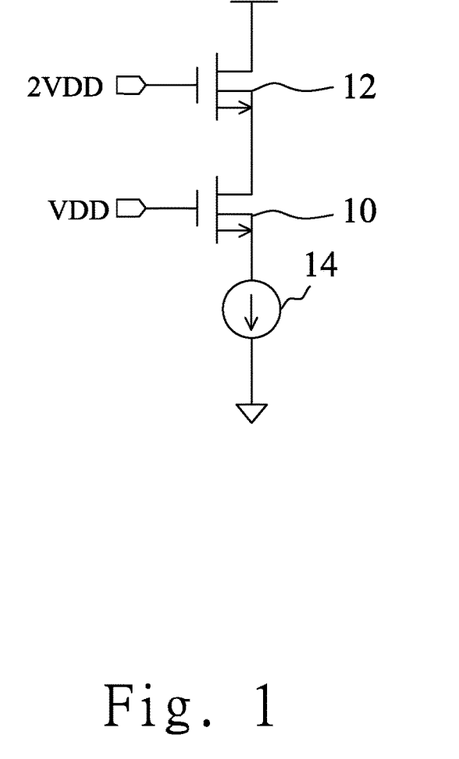
FIG. 1 is a circuit diagram of cascoded MOSFETs of the present invention.

In the present invention, MOSFETs are electrically cascoded to implement the circuit which can be produced with a low-voltage manufacturing process and is able to withstand high voltage. In this embodiment, NMOSFET is taken as an example for illustration. As shown in FIG. 1, a n-channel metal-oxide-semiconductor field-effect transistor (abbreviated as NMOSFET hereafter) 10 is electrically cascoded with a NMOSFET 12 and electrically connected to a current source 14. Particularly, each of the NMOSFETs 10 and 12 includes a gate and a source, and the source of the NMOSFET 10 is electrically connected to the drain of the NMOSFET 12, the current provided from the current source 14 flows through the NMOSFETs 10 and 12. When the current flowing through the NMOSFETs 10 and 12 is zero, the sources of the NMOSFETs 10 and 12 are charged by leakage current from the gate of the NMOSFETs 10 and 12, respectively, so that in each of the NMOSFETs 10 and 12, the source voltage is equal to the gate voltage and each of the NMOSFETs 10 and 12 is operated in a cut-off region. When the gate voltage is equal to a power voltage (abbreviated as VDD hereafter), the source voltage is also equal to the VDD. When the current flowing through the NMOSFETs 10 and 12 is not zero, the source voltage of each NMOSFET with a higher aspect ratio can be designed as about VDD−Vth, wherein Vth is a threshold voltage of the NMOSFET 10 or the NMOSFET 12. The source voltage is determined by the gate voltage, and the drain voltage of the NMOSFET 10 is determined by the source voltage of the NMOSFET 12 cascoded with the NMOSFET 10. As shown in FIG. 1, the drain voltage of the NMOSFET 10 is about double power voltage (abbreviated as 2VDD hereafter) minus the Vth. As a result, the voltage across two terminals of all terminals of each NMOSFET can be designed to be lower than a breakdown voltage of the NMOSFET, thereby achieving the objective of enable the NMOSFET to withstand high voltage.

The above-mentioned operation principle can be applied to p-channel metal-oxide-semiconductor field-effect transistor (abbreviated as PMOSFET hereafter). The NMOSFET includes a deep N-well electrically connected to the source and the base thereof, so as to prevent the problem that over-voltage forms on gate oxide layer and P-well.

Please refer to FIGS. 2 to 5. The biomedical stimulation protection device of the present invention can be operated in a stimulation mode or a sampling mode. The biomedical stimulation protection device includes a current source 16, a first upper PMOSFET 18, a first adaptive bias circuit 20, six first stimulating MOSFETs 22, a first lower NMOSFET 24, a first detecting MOSFET 26, a second detecting MOSFET 28, a second upper PMOSFET 30, a second adaptive bias circuit 32, a second lower NMOSFET 34, six second stimulating MOSFETs 36, a third detecting MOSFET 38 and a fourth detecting MOSFET 40. The first detecting MOSFET 26 and the third detecting MOSFET 38 are PMOSFETs, and the second detecting MOSFET 28 and the fourth detecting MOSFET 40 are NMOSFETs. In the stimulation mode, the current source 16 receives a quadruple power voltage (abbreviated as 4VDD hereafter), to generate a stimulation current. The first upper PMOSFET 18 is electrically connected to the current source 16. In the stimulation mode, the first upper PMOSFET 16 receives a triple power voltage (abbreviated as 3VDD hereafter) and is turned on, and the stimulation current flows through the first upper PMOSFET 18. In the stimulation mode, the first adaptive bias circuit 20 receives VDD, 2VDD and 3VDD. For example, VDD can be 3.3 V. The six first stimulating MOSFETs 22 are electrically cascoded with each other and electrically cascoded with the first upper PMOSFET 18, and is also electrically connected to the first adaptive bias circuit 20. A first central node n1 among the six first stimulating MOSFETs 22 includes a first output terminal electrically connected to the physiological tissue 42. In the stimulation mode, the first adaptive bias circuit 20 applies VDD, 2VDD and 3VDD to turn on the first stimulating MOSFETs 22 disposed between the first central node n1 and the first upper PMOSFET 18, so as to transmit the stimulation current to the physiological tissue 42, and form a first output voltage at the first output terminal. The first lower NMOSFET 24 is electrically connected to ground, the six first stimulating MOSFETs 22 are electrically cascoded between the first upper PMOSFET 18 and the first lower NMOSFET 24. In the stimulation mode, the first lower NMOSFET 24 receives zero voltage GND and is turned off, so as to block the stimulation current from flowing to ground. For example, VDD can be 6 times of a threshold voltage of each of the first upper PMOSFET 18, the six first stimulating MOSFETs 22 and the first lower NMOSFET 24. The first adaptive bias circuit 20 can control, according to VDD, 2VDD, 3VDD and the first output voltage, a voltage difference at two terminals of each of the first upper PMOSFET 18, the six first stimulating MOSFETs 22 and the first lower NMOSFET 24 to be lower than or equal to VDD.

The first detecting MOSFET 26 is electrically connected to the first adaptive bias circuit 20 and the first stimulating MOSFET 22. In the stimulation mode, the first detecting MOSFET 26 is turned off. In the sampling mode, the first detecting MOSFET 26 is turned on and receives an external voltage which is equal to VDD. The second detecting MOSFET 28 is electrically connected to the first stimulating MOSFET 22 and the signal detector 44. In the stimulation mode, the second detecting MOSFET 28 is turned off. In the sampling mode, the second detecting MOSFET 28 is turned on, and the current source 16 receives zero voltage GND, and stops generating the stimulation current, so the first upper PMOSFET 18 receives zero voltage GND and is turned off, the first adaptive bias circuit 20 receives zero voltage GND, the first lower NMOSFET 24 receives zero voltage GND and is turned off. The first detecting MOSFET 26 uses the external voltage to drive the first adaptive bias circuit 20 to turn on the first stimulating MOSFETs 22 disposed between the first central node n1 and the first lower NMOSFET 24, thereby using the first stimulating MOSFETs 22 and the second detecting MOSFET 28 disposed between the first central node n1 and the first lower NMOSFET 24 to transmit a first physiological current from the physiological tissue 42 to the signal detector 44.

The second upper PMOSFET 30 receives 4VDD and is turned off, so as to block the stimulation current from flowing the second upper PMOSFET 30. In the stimulation mode, the second adaptive bias circuit 32 receives VDD, 2VDD and 3VDD. The second lower NMOSFET 34 is electrically connected to ground. In the stimulation mode, the second lower NMOSFET 34 receives VDD and is turned on. The second stimulating MOSFETs 36 electrically cascoded with each other, and electrically cascoded between the second upper PMOSFET 30 and the second lower NMOSFET 34. The second stimulating MOSFETs 36 are electrically connected to a second adaptive bias circuit 32, and a second central node n2 among the second stimulating MOSFETs 36 includes a second output terminal electrically connected to a physiological tissue 42. In the stimulation mode, the second adaptive bias circuit 32 applies VDD, 2VDD and 3VDD to turn on the second stimulating MOSFETs 36 disposed between the second central node n2 and the second lower NMOSFET 34, so as to transmit the stimulation current from physiological tissue 42 to ground through the second lower NMOSFET 34, and form a second output voltage at the second output terminal. For example, VDD can be 6 times of a threshold voltage of each of the second upper PMOSFET 30, the second stimulating MOSFETs 36, and the second lower NMOSFET 34. According to the VDD, the 2VDD, the 3VDD and the second output voltage, the second adaptive bias circuit 32 can control a voltage difference at two terminals of each of the second upper PMOSFET 30, the second stimulating MOSFETs 36 and the second lower NMOSFET 34, to be lower than or equal to VDD.

The third detecting MOSFET 38 is electrically connected to the second adaptive bias circuit 32 and the second stimulating MOSFET 36. In the stimulation mode, the third detecting MOSFET 38 is turned off. In the sampling mode, the third detecting MOSFET 38 is turned on and receives an external voltage. The fourth detecting MOSFET 40 is electrically connected to the second stimulating MOSFET 36 and the signal detector 44. In the stimulation mode, the fourth detecting MOSFET 40 is turned off. In the sampling mode, the fourth detecting MOSFET 40 is turned on, and the current source 16 receives zero voltage GND and stops generating the stimulation current. The second upper PMOSFET 30 receives 4VDD and is turned off, the second adaptive bias circuit 32 receives zero voltage GND, and the second lower NMOSFET 34 receives zero voltage GND and is turned off, the third detecting MOSFET 38 uses the external voltage to drive the second adaptive bias circuit 32, to turn on the second stimulating MOSFETs 36 disposed between the second central node n2 and the second lower NMOSFET 34, so that the second stimulating MOSFETs 36 and the fourth detecting MOSFET 40 disposed between the second central node n2 and the second lower NMOSFET 34 are used to transmit a second physiological current from the physiological tissue 42 to the signal detector 44.

Figure 2:
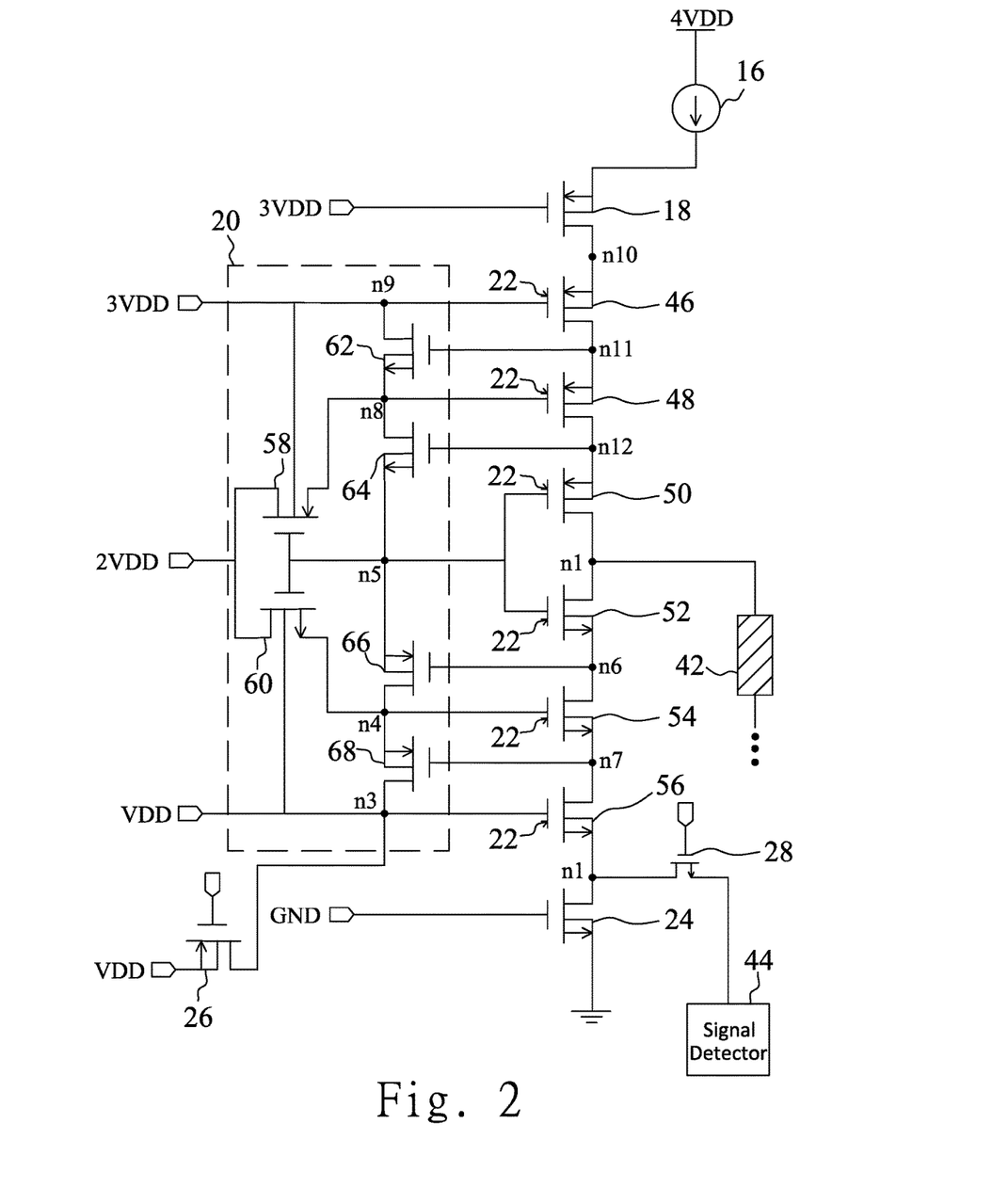
FIG. 2 is a circuit diagram of a first adaptive bias circuit and a first stimulating MOSFET operated in a stimulation mode, according to the present invention.
Figure 4:
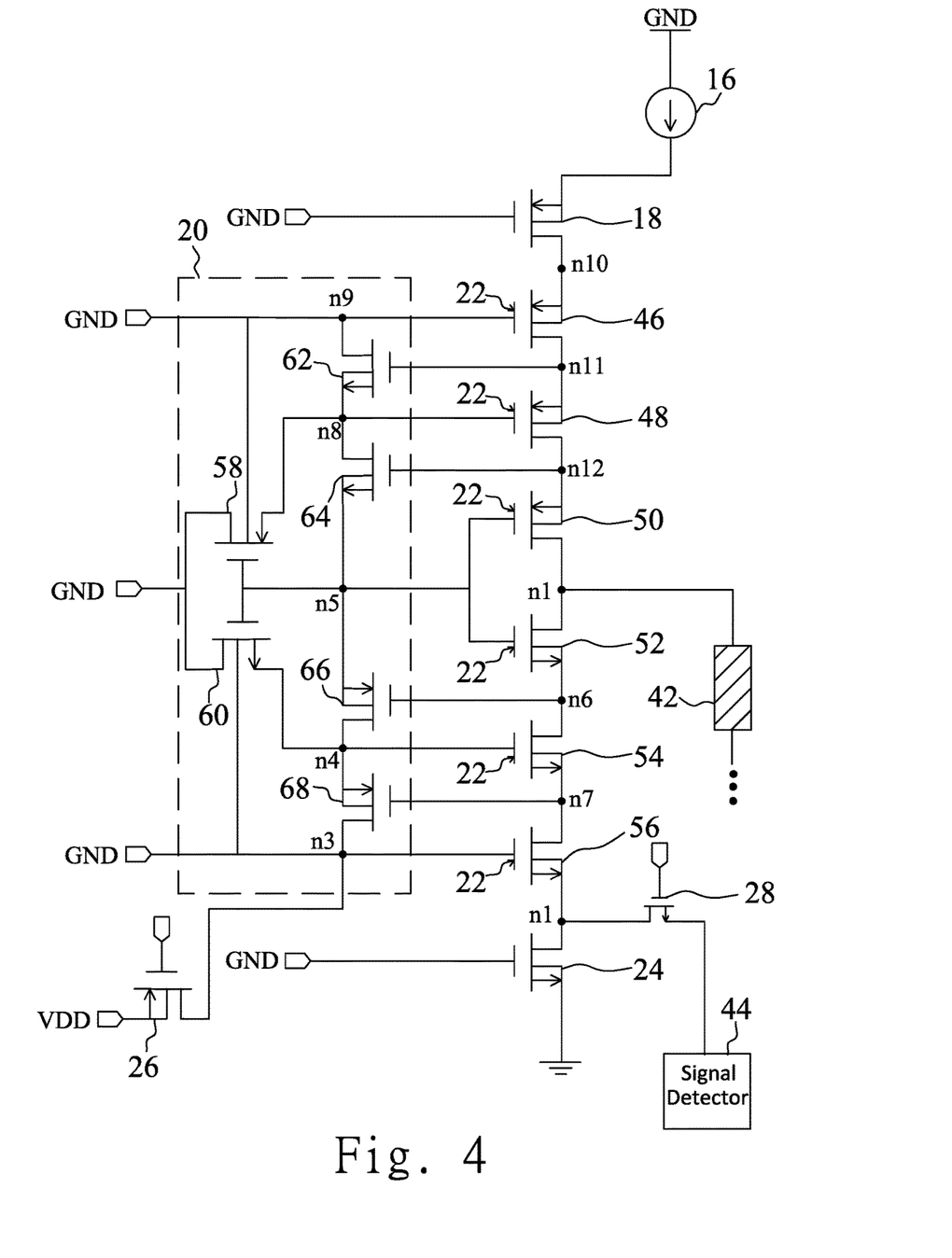
FIG. 4 is a circuit diagram of the first adaptive bias circuit and the first stimulating MOSFETs operated in a sampling mode, according to the present invention.

Particularly, the gate of the first upper PMOSFET 18 receives 3VDD or zero voltage, the source of the first upper PMOSFET 18 is electrically connected to the current source 16. The first stimulating MOSFETs 22 can comprise a first PMOSFET 46, a second PMOSFET 48, a third PMOSFET 50, a first NMOSFET 52, a second NMOSFET 54 and a third NMOSFET 56. The source of the first PMOSFET 46 is electrically connected to the drain of the first upper PMOSFET 18, and the gate of the first PMOSFET 46 receives 3VDD or zero voltage GND. The source of the second PMOSFET 48 is electrically connected to the drain of the first PMOSFET 46, the gate of the second PMOSFET 48 is electrically connected to the first adaptive bias circuit 20. The source of the third PMOSFET 50 is electrically connected to the drain of the second PMOSFET 48, the gate of the third PMOSFET 50 is electrically connected to the first adaptive bias circuit 20, the drain of the third PMOSFET 50 is electrically connected to the first central node n1. The drain of the first NMOSFET 52 is electrically connected to the first central node n1, the gate of the first NMOSFET 52 is electrically connected to the gate of the third PMOSFET 50 and the first adaptive bias circuit 20. The drain of the second NMOSFET 54 is electrically connected to the source of the first NMOSFET 52, the gate of the second NMOSFET 54 is electrically connected to the first adaptive bias circuit 20. The drain of the third NMOSFET 56 is electrically connected to the source of the second NMOSFET 54, the gate of the third NMOSFET 56 receives VDD or zero voltage GND, the source of the third NMOSFET 56 is electrically connected to the drain of the first lower NMOSFET 24 and the second detecting MOSFET 28. The gate of the third NMOSFET 56 is electrically connected to the first detecting MOSFET 26 and the first adaptive bias circuit 20, the gate of the first lower NMOSFET 24 receives zero voltage GND, and the source of the first lower NMOSFET 24 is electrically connected to ground. In the stimulation mode, the first adaptive bias circuit 20 applies VDD, 2VDD and 3VDD to turn on the first PMOSFET 46, the second PMOSFET 48 and the third PMOSFET 50. For example, VDD can be six times of a threshold voltage of each of the first PMOSFET 46, the second PMOSFET 48, the third PMOSFET 50, the first NMOSFET 52, the second NMOSFET 54 and the third NMOSFET 56. According to VDD, 2VDD, 3VDD and the first output voltage, the first adaptive bias circuit 20 can control a voltage difference at two terminals of each of the first PMOSFET 46, the second PMOSFET 48, the third PMOSFET 50, the first NMOSFET 52, the second NMOSFET 54 and the third NMOSFET 56 to be lower than or equal to VDD. In the sampling mode, the first detecting MOSFET 26 applies the external voltage to drive the first adaptive bias circuit 20, to turn on the first NMOSFET 52, the second NMOSFET 54 and the third NMOSFET 56, so as to use the first NMOSFET 52, the second NMOSFET 54 and the third NMOSFET 56 to transmit the first physiological current to the signal detector 44.

The first adaptive bias circuit 20 can include a fourth PMOSFET 58, a fourth NMOSFET 60, a fifth NMOSFET 62, a sixth NMOSFET 64, a fifth PMOSFET 66 and a sixth PMOSFET 68. The drain of the fourth PMOSFET 58 receives 2VDD or zero voltage GND. The drain of the fourth NMOSFET 60 receives 2VDD or zero voltage GND, and the gate of the fourth NMOSFET 60 is electrically connected to the gate of the fourth PMOSFET 58. The drain of the fifth NMOSFET 62 receives 3VDD or zero voltage GND, the drain and the gate of the fifth NMOSFET 62 are electrically connected the gate and the drain of the first PMOSFET 46, respectively. The source of the fifth NMOSFET 62 is electrically connected to the source of the fourth PMOSFET 58 and the gate of the second PMOSFET 48. The drain of the sixth NMOSFET 64 is electrically connected to the source of the fifth NMOSFET 62, the gate of the sixth NMOSFET 64 is electrically connected to the drain of the second PMOSFET 48, the source of the sixth NMOSFET 64 is electrically connected to the gates of the fourth PMOSFET 58, the third PMOSFET 50 and the first NMOSFET 52. The source of the fifth PMOSFET 66 is electrically connected to the source of the sixth NMOSFET 64, the gate of the fifth PMOSFET 66 is electrically connected to the source of the first NMOSFET 52, the drain of the fifth PMOSFET 66 is electrically connected to the source of the fourth NMOSFET 60 and the gate of the second NMOSFET 54, the base of the fifth PMOSFET 66 is electrically connected to the source of the fifth PMOSFET 66. The fifth PMOSFET 66 includes a first parasitic body-drain diode. The source of the sixth PMOSFET 68 is electrically connected to the drain of the fifth PMOSFET 66, the gate of the sixth PMOSFET 68 is electrically connected to the source of the second NMOSFET 54, the drain of the sixth PMOSFET 68 is electrically connected to the gate of the third NMOSFET 56 and the first detecting MOSFET 26. The base of the sixth PMOSFET 68 is electrically connected to the source of the sixth PMOSFET 68, and the sixth PMOSFET 68 includes a second parasitic body-drain diode. For example, VDD can be four to five times of a forward-biased voltage of each of the first parasitic body-drain diode and the second parasitic body-drain diode. The drain of the sixth PMOSFET 68 receives VDD or zero voltage GND. In the stimulation mode, the fourth PMOSFET 58, the fourth NMOSFET 60, the fifth NMOSFET 62, the sixth NMOSFET 64, the fifth PMOSFET 66 and the sixth PMOSFET 68 turn on the first PMOSFET 46, the second PMOSFET 48 and the third PMOSFET 50 according to VDD, 2VDD and 3VDD. In this embodiment, VDD can be 6 times of a threshold voltage of each of the fourth PMOSFET 58, the fourth NMOSFET 60, the fifth NMOSFET 62, the sixth NMOSFET 64, the fifth PMOSFET 66 and the sixth PMOSFET 68. VDD, 2VDD, 3VDD and the first output voltage can be applied to the first PMOSFET 46, the second PMOSFET 48, the third PMOSFET 50, the first NMOSFET 52, the second NMOSFET 54 and the third NMOSFET 56, to control a voltage difference at two terminals of each of the fourth PMOSFET 58, the fourth NMOSFET 60, the fifth NMOSFET 62, the sixth NMOSFET 64, the fifth PMOSFET 66 and the sixth PMOSFET 68, to be lower than or equal to VDD. In the sampling mode, the first detecting MOSFET 26 applies the external voltage to drive the fifth PMOSFET 66 and the sixth PMOSFET 68 to turn on the first NMOSFET 52, the second NMOSFET 54 and the third NMOSFET 56.

Figure 3:
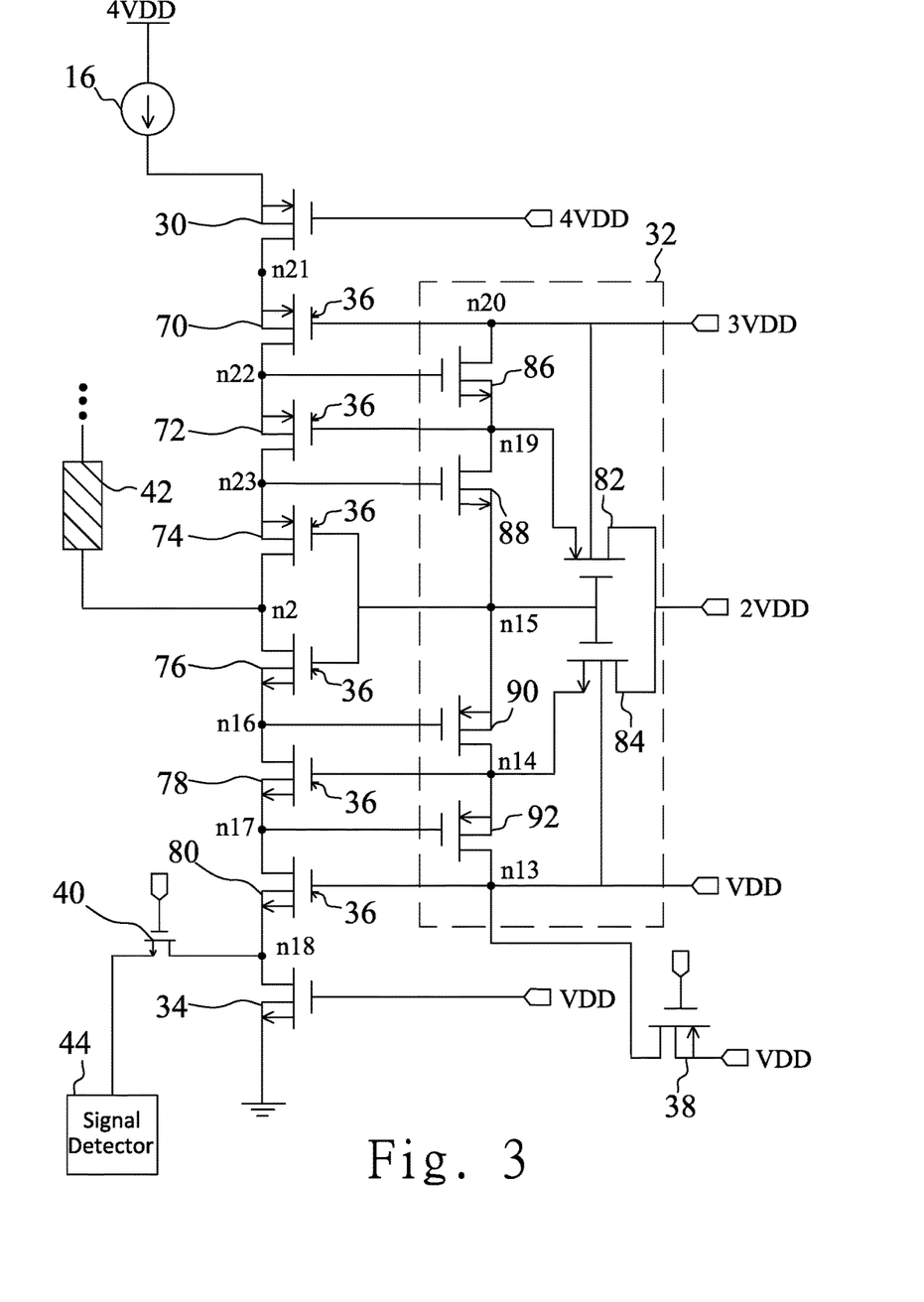
FIG. 3 is a circuit diagram of a second adaptive bias circuit and second stimulating MOSFETs operated in the stimulation mode, according to the present invention.
Figure 5:
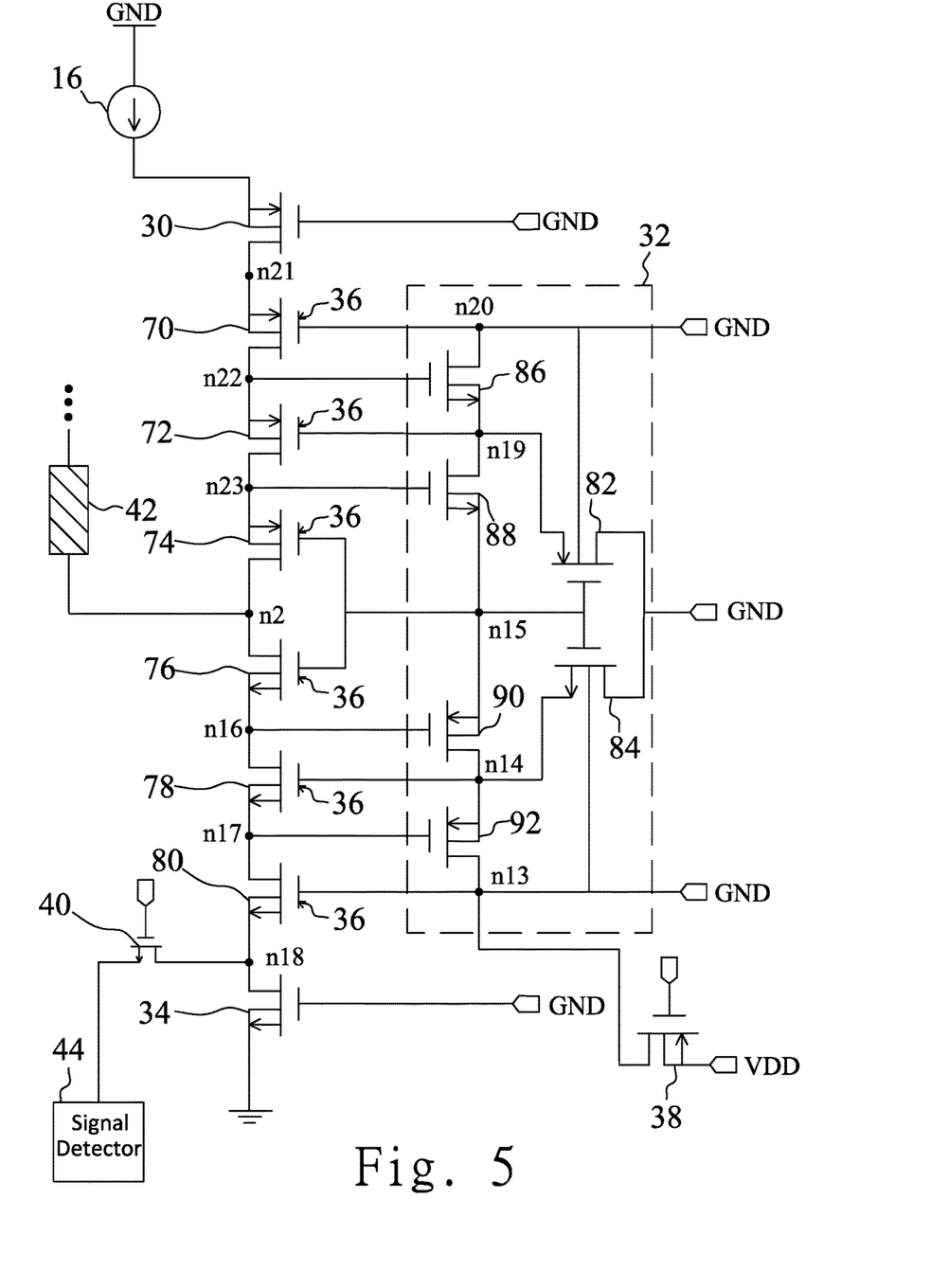
FIG. 5 is a circuit diagram of the second adaptive bias circuit and the second stimulating MOSFETs operated in a sampling mode, according to the present invention.

The gate of the second upper PMOSFET 30 receives 4VDD or zero voltage GND, and the source of the second upper PMOSFET 30 is electrically connected to the current source 16. The second stimulating MOSFETs 36 can comprise a seventh PMOSFET 70, an eighth PMOSFET 72, a ninth PMOSFET 74, a seventh NMOSFET 76, an eighth NMOSFET 78 and a ninth NMOSFET 80. The source of the seventh PMOSFET 70 is electrically connected to the drain of the second upper PMOSFET 30, the gate of the seventh PMOSFET 70 receives 3VDD or zero voltage GND. The source of the eighth PMOSFET 72 is electrically connected to the drain of the seventh PMOSFET 70, the gate of the eighth PMOSFET 72 is electrically connected to the second adaptive bias circuit 32. The source of the ninth PMOSFET 74 is electrically connected to the drain of the eighth PMOSFET 72, the gate of the ninth PMOSFET 74 is electrically connected to the second adaptive bias circuit 32, and the drain of the ninth PMOSFET 74 is electrically connected to a second central node n2. The drain of the seventh NMOSFET 76 is electrically connected to the second central node n2, the gate of the seventh NMOSFET 76 is electrically connected to the gate of the ninth PMOSFET 74 and the second adaptive bias circuit 32. The drain of the eighth NMOSFET 78 is electrically connected to the source of the seventh NMOSFET 76, the gate of the eighth NMOSFET 78 is electrically connected to the second adaptive bias circuit 32. The drain of the ninth NMOSFET 80 is electrically connected to the source of the eighth NMOSFET 78, the gate of the ninth NMOSFET 80 receives VDD or zero voltage GND, the source of the ninth NMOSFET 80 is electrically connected to the drain of the second lower NMOSFET 34 and the fourth detecting MOSFET 40, the gate of the ninth NMOSFET 80 is electrically connected to the third detecting MOSFET 38 and the second adaptive bias circuit 32. The gate of the second lower NMOSFET 34 receives VDD, and the source of the second lower NMOSFET 34 is electrically connected to ground. In the stimulation mode, the second adaptive bias circuit 32 turns on the seventh NMOSFET 76, the eighth NMOSFET 78 and the ninth NMOSFET 80 according to VDD, 2VDD and 3VDD. In this embodiment, VDD can be 6 times of a threshold voltage of each of the seventh PMOSFET 70, the eighth PMOSFET 72, the ninth PMOSFET 74, the seventh NMOSFET 76, the eighth NMOSFET 78 and the ninth NMOSFET 80. According to VDD, 2VDD, 3VDD and a second output voltage, the second adaptive bias circuit 32 can control a voltage difference at two terminals of each of the seventh PMOSFET 70, the eighth PMOSFET 72, the ninth PMOSFET 74, the seventh NMOSFET 76, the eighth NMOSFET 78 and the ninth NMOSFET 80, to be lower than or equal to the VDD. In the sampling mode, the third detecting MOSFET 38 can apply the external voltage to drive the second adaptive bias circuit 32, to turn on the seventh NMOSFET 76, the eighth NMOSFET 78 and the ninth NMOSFET 80, so as to use the seventh NMOSFET 76, the eighth NMOSFET 78 and the ninth NMOSFET 80 to transmit the second physiological current to the signal detector 44.

The second adaptive bias circuit 32 can include a tenth PMOSFET 82, a tenth NMOSFET 84, an eleventh NMOSFET 86, a twelfth NMOSFET 88, an eleventh PMOSFET 90 and a twelfth PMOSFET 92. The drain of the tenth PMOSFET 82 receives 2VDD or zero voltage GND. The drain of the tenth NMOSFET 84 receives 2VDD or zero voltage GND, the gate of the tenth NMOSFET 84 is electrically connected to the gate of the tenth PMOSFET 82. The drain of the eleventh NMOSFET 86 receives 3VDD or zero voltage GND, the drain and the gate of the eleventh NMOSFET 86 are electrically connected to the gate and the drain of the seventh PMOSFET 70, respectively. The source of the eleventh NMOSFET 86 is electrically connected to the source of the tenth PMOSFET 82 and the gate of the eighth PMOSFET 72. The drain of the twelfth NMOSFET 88 is electrically connected to the source of the eleventh NMOSFET 86, the gate of the twelfth NMOSFET 88 is electrically connected to the drain of the eighth PMOSFET 72, the source of the twelfth NMOSFET 88 is electrically connected to the gates of the tenth PMOSFET 82, the ninth PMOSFET 74 and the seventh NMOSFET 76. The source of the eleventh PMOSFET 90 is electrically connected to the source of the twelfth NMOSFET 88, the gate of the eleventh PMOSFET 90 is electrically connected to the source of the seventh NMOSFET 76, the drain of the eleventh PMOSFET 90 is electrically connected to the source of the tenth NMOSFET 84 and the gate of the eighth NMOSFET 78, and the base of the eleventh PMOSFET 90 is electrically connected to the source of the eleventh PMOSFET 90. The eleventh PMOSFET 90 comprises a third parasitic body-drain diode. The source of the twelfth PMOSFET 92 is electrically connected to the drain of the eleventh PMOSFET 90, the gate of the twelfth PMOSFET 92 is electrically connected to the source of the eighth NMOSFET 78, the drain of the twelfth PMOSFET 92 is electrically connected to the gate of the ninth NMOSFET 80 and the third detecting MOSFET 38, and the base of the twelfth PMOSFET 92 is electrically connected to the source of the twelfth PMOSFET 92. The twelfth PMOSFET 92 comprises a fourth parasitic body-drain diode. For example, VDD is four to five times of a forward-biased voltage of each of the third parasitic body-drain diode and the fourth parasitic body-drain diode. The drain of the twelfth PMOSFET 92 receives VDD or zero voltage GND. In the stimulation mode, the tenth PMOSFET 82, the tenth NMOSFET 84, the eleventh NMOSFET 86, the twelfth NMOSFET 88, the eleventh PMOSFET 90 and the twelfth PMOSFET 92 turn on the seventh NMOSFET 76, the eighth NMOSFET 78 and the ninth NMOSFET 80 according to VDD, 2VDD and 3VDD. In this embodiment, VDD can be 6 times of a threshold voltage of each of the tenth PMOSFET 82, the tenth NMOSFET 84, the eleventh NMOSFET 86, the twelfth NMOSFET 88, the eleventh PMOSFET 90 and the twelfth PMOSFET 92. VDD, 2VDD, 3VDD and the second output voltage can be applied to the seventh PMOSFET 70, the eighth PMOSFET 72, the ninth PMOSFET 74, the seventh NMOSFET 76, the eighth NMOSFET 78 and the ninth NMOSFET 80, to control a voltage difference at two terminals of each of the tenth PMOSFET 82, the tenth NMOSFET 84, the eleventh NMOSFET 86, the twelfth NMOSFET 88, the eleventh PMOSFET 90 and the twelfth PMOSFET 92 to be lower than or equal to VDD. In the sampling mode, the third detecting MOSFET 38 applies the external voltage to drive the eleventh PMOSFET 90 and the twelfth PMOSFET 92 to turn on the seventh NMOSFET 76, the eighth NMOSFET 78 and the ninth NMOSFET 80.

The present invention uses the adaptive bias circuit to detect the output voltage, to generate an appropriate bias voltage, and provide the bias voltage to the stimulating MOSFETs, so that the voltage difference at any two terminals of each MOSFET can be lower than or equal to the withstand voltage defined in low-voltage manufacturing process, thereby effectively preventing the stimulating MOSFETs and the MOSFETs of the adaptive bias circuit from being damaged by high voltage.

Please refer to FIG. 2. The stimulation mode of the biomedical stimulation protection device of the present invention is described in the following paragraphs, and the threshold voltage of each MOSFET is Vth.

First, when the stimulation current provided from the current source 16 is slightly higher than zero, the first output voltage and the second output voltage are about zero voltage GND. In the other words, the voltages at the nodes n1 and n2 are about zero voltage GND. Since the voltage at the node n3 is VDD, the third NMOSFET 56 is turned on by VDD, and the voltages at the nodes n4 and n5 rise to be higher than zero voltage GND and lower than VDD through the parasitic body-drain diodes of the sixth PMOSFET 68 and the fifth PMOSFET 66, so as to turn on the first NMOSFET 52 and the second NMOSFET 54. As a result, the voltages at the nodes n6, n7 and n8 are about zero voltage GND. The stimulation current cannot flow through the first NMOSFET 52, the second NMOSFET 54, the third NMOSFET and the first lower NMOSFET 24, so the first NMOSFET 52, second NMOSFET 54, and the drain of the first lower NMOSFETZ 56 are operated in linear region. The voltages at the nodes n6 and n7 are about zero voltage GND, the sixth PMOSFET 68 and the fifth PMOSFET 66 can be turned on, and voltages at the nodes n4 and n5 continuously rise to VDD, so as to operate the sixth PMOSFET 68 and the fifth PMOSFET 66 in the linear region. Since the voltages at the nodes n4 and n5 are VDD, the fourth NMOSFET 60 is operated in cut-off region. Since the drain-gate voltage of the fourth PMOSFET 58 is VDD, the fourth PMOSFET 58 is turned on. The voltage at the node n8 is 2VDD, and the fourth PMOSFET 58 is operated in the linear region. The stimulation current is slightly higher than zero and the first output voltage is low enough, so the first PMOSFET 46, the second PMOSFET 48 and the third PMOSFET 50 are operated in a saturation region. Since the voltage at the node n9 is 3VDD, the voltages at the nodes n10, n11 and n12 are 3VDD+Vth, 2VDD+Vth, and VDD+Vth, respectively. As a result, the fifth NMOSFET 62 and the sixth NMOSFET 64 are also operated in the saturation region.

When the stimulation current provided from the current source 16 continuously increases, the first output voltage and the second output voltage are about VDD and zero voltage GND, respectively. In the other words, voltages at the nodes n1 and n2 are about VDD and zero voltage GND, respectively. Since the first NMOSFET 52, the second NMOSFET 54 and the third NMOSFET 56 are originally operated in the linear region, the voltages at the nodes n6, n7 and n8 rise to VDD. Since the voltages at the nodes n8 and n3 are VDD, the third NMOSFET 56 is operated in the cut-off region, the first NMOSFET 52 and the second NMOSFET 54 are still operated in the linear region. In order to operate the second NMOSFET 54 in the linear region, the voltage at node n4 is risen to VDD+Vth, so that the sixth PMOSFET 68 is operated in the saturation region, the fifth PMOSFET 66 is still operated in the linear region, and the voltage at the node n5 is VDD+Vth. Since the voltages at the nodes n4 and n5 are VDD+Vth, the fourth NMOSFET 60 is operated in the cut-off region. The voltage at the node n5 is VDD+Vth, but the voltage at the node n5 does not affect the state of the fourth PMOSFET 58; as a result, the fourth PMOSFET 58 is still operated in the linear region, and the voltage at the node n8 is 2VDD. The stimulation current continuously increases and the first output voltage is low enough, so the first PMOSFET 46, the second PMOSFET 48 and the third PMOSFET 50 are operated in the saturation region, and the voltages at the nodes n10, n11 and n12 are 3VDD+Vth, 2VDD+Vth and VDD+2Vth, respectively. As a result, the fifth NMOSFET 62 and the sixth NMOSFET 56 are operated in saturation region.

When the stimulation current provided from the current source 16 continuously increases, the first output voltage and the second output voltage are about 2VDD and zero voltage GND, respectively. In the other words, voltages at the nodes n1 and n2 are about 2VDD and zero voltage GND. Since the first NMOSFET 52 and the second NMOSFET 54 are originally operated in the linear region, the voltages at the nodes n6 and n7 rise to 2VDD. Since the voltage at the node n7 is higher than the voltage at the node n4, the sixth PMOSFET 68 is operated in the cut-off region. Since the sixth PMOSFET 68 is operated in the cut-off region, the voltage at the node n4 rises to 2VDD, and the second NMOSFET 54 is turned off. Since the first NMOSFET 52 is still operated in the linear region, the voltage at the node n5 rises to 2VDD+Vth, and the fourth NMOSFET is operated in a subthreshold region. Since the voltage at node n5 rises to 2VDD+Vth, the voltage at the node n8 can be higher than the voltage at the node n5, and the fourth PMOSFET 58 is operated in the saturation region. Since the fourth PMOSFET 58 is operated in the saturation region, the voltage at the node n8 can be 2VDD+2Vth. Since the stimulation current continuously increases and first output voltage is low enough, the first PMOSFET 46, the second PMOSFET 48 and the third PMOSFET 50 are operated in the saturation region, and the voltages at the nodes n10, n11 and n12 are 3VDD+Vth, 2VDD+3Vth and 2VDD+2Vth, respectively. As a result, the fifth NMOSFET 62 and the sixth NMOSFET 64 are operated in the saturation region.

When the stimulation current provided from the current source 16 continuously increases, the first output voltage and the second output voltage are about 3VDD and zero voltage GND, respectively. In the other words, the voltages at the nodes n1 and n2 are about 3VDD and zero voltage GND. Since first NMOSFET 52 is originally operated in the linear region, VDD can rise the voltage at the node n6 to 3VDD. Since the voltage at the node n6 is higher than the voltage at the node n5, the fifth PMOSFET 66 is operated in the cut-off region. Since the fifth PMOSFET 66 is operated in the cut-off region, the voltage at the node n5 rises to 3VDD, so that the first NMOSFET 52 is turned off and the fourth NMOSFET 60 is operated in the linear region. The voltages at the node n5 and n9 are 3VDD, so that the voltage at the node n8 is also 3VDD, and the fourth PMOSFET 58 is operated in the cut-off region, and the fifth NMOSFET 62 and the sixth NMOSFET 64 are operated in the linear region. The fifth NMOSFET 62, and the sixth NMOSFETZ 64 are operated in the linear region, so the voltages at the nodes n10, n11 and n12 are 3VDD+Vth, 3VDD+Vth, and 3VDD+Vth, respectively, and the first PMOSFET 46 and the second PMOSFET 48 are operated in the linear region, and the third PMOSFET 50 is operated in the saturation region.

When the stimulation current provided from the current source 16 continuously increases, the first output voltage and the second output voltage are about 4VDD and zero voltage GND, respectively. In the other words, voltages at the nodes n1 and n2 are about 4VDD and zero voltage GND. The first output voltage can rise the voltages at the nodes n10, n11 and n12 to 4VDD, so that the third PMOSFET 50 can be operated on the linear region and remaining MOSFETs are maintained in original state.

Please refer to FIG. 3. The operations of the second stimulating MOSFETs 36 and second adaptive bias circuit 32 in the stimulation mode is described in the following paragraphs. Since the voltage at the node n13 is VDD, the ninth NMOSFET 80 can be turned on by VDD, and the voltages at the nodes n14 and n15 can rise to be higher than zero voltage GND and lower than the VDD through the parasitic body-drain diodes of the eleventh PMOSFET 90 and the twelfth PMOSFET 92, so that the seventh NMOSFET 76 and the eighth NMOSFET 78 are turned on. The voltages at the nodes n16, n17 and n18 are about zero voltage GND, and the seventh NMOSFET 76, the eighth NMOSFET 78, and the ninth NMOSFET 80 are operated in the linear region. Since the voltages at the node n16 and n17 are about zero voltage GND, the eleventh PMOSFET 90 and the twelfth PMOSFET 92 are turned on, and the voltages at the node n14 and n15 continuously rise to VDD, so that the eleventh PMOSFET 90 and the twelfth PMOSFET 92 can be operated in the linear region. Since the voltage at the node n15 is VDD, the tenth NMOSFET 84 and the tenth PMOSFET 82 are operated in the cut-off region and the linear region, respectively, and the voltage at the node n19 rises to 2VDD. The stimulation current does not flow through the seventh PMOSFET 70, the eighth PMOSFET 72, the ninth PMOSFET 74, the eleventh NMOSFET 86 and the twelfth NMOSFET 88, so the gate-source voltages of the seventh PMOSFET 70, the eighth PMOSFET 72, the ninth PMOSFET 74, the eleventh NMOSFET 86 and the twelfth NMOSFET 88 are zero voltage. Furthermore, the voltage at the node n20 is 3VDD, and the voltages at the nodes n21, n22 and n23 are 3VDD, 2VDD and VDD, respectively.

Please refer to FIG. 4. The operations of the first stimulating MOSFETs 22 and first adaptive bias circuit 20 in the sampling mode are described in the following paragraphs. The first adaptive bias circuit 20 and the first PMOSFET 46 receive zero voltage, so the first PMOSFET 46, the second PMOSFET 48, the fourth PMOSFET 58, the fourth NMOSFET 60, the fifth NMOSFET 62 and the sixth NMOSFET 64 are operated in the cut-off region, and the third PMOSFET 50 can be operated on the cut-off region. Furthermore, the first detecting MOSFET 26 uses the external voltage to rise the voltage at the node n3, and also rise the voltages at the nodes n4 and n5 through the parasitic body-drain diodes of the fifth PMOSFET 66 and the sixth PMOSFET 68, so that first NMOSFET 52, the second NMOSFET 54, and the third NMOSFET 56 are operated in the linear region, and the fifth PMOSFET 66 and the sixth PMOSFET 68 can be turned on. As a result, the first NMOSFET 52, the second NMOSFET 54, the third NMOSFET 56 and the second detecting MOSFET 28 can transmit the first physiological current from the physiological tissue 42 to the signal detector 44.

Please refer to FIG. 5. The operations of the second stimulating MOSFETs 36 and the second adaptive bias circuit 32 in the sampling mode are described in the following paragraphs. The second adaptive bias circuit 32 and the seventh PMOSFET 70 receive zero voltage, so the seventh PMOSFET 70, the eighth PMOSFET 72, the tenth PMOSFET 82, the tenth NMOSFET 84, the eleventh NMOSFET 86 and the twelfth NMOSFET 88 are operated in the cut-off region, to make the ninth PMOSFET 74 operate in the cut-off region. Furthermore, the third detecting MOSFET 38 can use the external voltage to rise the voltage at the node n13, and rise the voltages at the node n14 and n15 through the parasitic body-drain diodes of the eleventh PMOSFET 90 and the twelfth PMOSFET 92, so that the seventh NMOSFET 76, the eighth NMOSFET 78, and the ninth NMOSFET 80 can be operated in the linear region, to turn on the eleventh PMOSFET 90 and the twelfth PMOSFET 92. As a result, the seventh NMOSFET 76, the eighth NMOSFET 78, the ninth NMOSFET 80 and the fourth detecting MOSFET 40 can transmit the second physiological current from the physiological tissue 42 to the signal detector 44.

According to above-mentioned content, the present invention use the adaptive bias circuit to detect the output voltage, to generate an appropriate bias voltage, and provide the bias voltage to the stimulating MOSFETs, so as to control the voltage difference at any two terminals of each MOSFET to be lower than or equal to the withstand voltage of low-voltage manufacturing process, thereby effectively preventing the stimulating MOSFETs, the adaptive bias circuit and a back-end signal detection circuit from being damaged by high voltage.

The present invention disclosed herein has been described by means of specific embodiments. However, numerous modifications, variations and enhancements can be made thereto by those skilled in the art without departing from the spirit and scope of the disclosure set forth in the claims.

What is claimed is:

1. A biomedical stimulation protection device, operating in a stimulation mode or a sampling mode, and the biomedical stimulation protection device comprising:
    a current source configured to receive a quadruple power voltage (4VDD) in the stimulation mode, to generate a stimulation current;
    a first upper p-channel metal-oxide-semiconductor field-effect transistor (PMOSFET) electrically connected to the current source, wherein, in the stimulation mode, the first upper PMOSFET receives a triple power voltage (3VDD) and is turned on, and the stimulation current flows through the first upper PMOSFET;
    a first adaptive bias circuit configured to receive a power voltage (VDD), a double power voltage (2VDD) and 3VDD in the stimulation mode; and
    six first stimulating metal-oxide-semiconductor field-effect transistors (MOSFETs) electrically cascoded with each other and electrically cascoded the first upper PMOSFET, and electrically connected to the first adaptive bias circuit, wherein a first central node among the six first stimulating MOSFETs comprises a first output terminal electrically connected to a physiological tissue;
    wherein, in the stimulation mode, according to the VDD, 2VDD and 3VDD, the first adaptive bias circuit turns on at least one of the six first stimulating MOSFETs disposed between the first central node and the first upper PMOSFET, to transmit the stimulation current to the physiological tissue and form a first output voltage at the first output terminal, and the first adaptive bias circuit controls a voltage difference at two terminals of each of the first upper PMOSFET and the six first stimulating MOSFETs to be lower than or equal to the VDD according to the VDD, 2VDD, 3VDD and the first output voltage.

2. The biomedical stimulation protection device according to claim 1, wherein the VDD is 6 times of a threshold voltage of each of the first upper PMOSFET and the six first stimulating MOSFETs.

3. The biomedical stimulation protection device according to claim 2, further comprising a first lower n-channel metal-oxide-semiconductor field-effect transistor (NMOSFET) electrically connected to ground, wherein the six first stimulating MOSFETs are electrically cascoded between the first upper PMOSFET and the first lower NMOSFET, and in the stimulation mode, the first lower NMOSFET receives zero voltage and is turned off to block the stimulation current from flowing to ground, and the VDD is 6 times of a threshold voltage of the first lower NMOSFET, and the first adaptive bias circuit controls a voltage difference at two terminals of the first lower NMOSFET to be lower than or equal to the VDD according to the VDD, 2VDD, 3VDD and the first output voltage.

4. The biomedical stimulation protection device according to claim 3, further comprising:
   a first detecting MOSFET electrically connected to the first adaptive bias circuit and the first stimulating MOSFETs, wherein in the stimulation mode, the first detecting MOSFET is turned off, and in the sampling mode, the first detecting MOSFET is turned on and receives an external voltage, and the external voltage is equal to the VDD; and
   a second detecting MOSFET electrically connected to the six first stimulating MOSFETs and a signal detector, and in the stimulation mode, the second detecting MOSFET is turned off, and in the sampling mode, the second detecting MOSFET is turned on, and the current source receives zero voltage and stops generating the stimulation current, and the first upper PMOSFET receives zero voltage and is turned off, the first adaptive bias circuit receives zero voltage, the first lower NMOSFET receives zero voltage and is turned off, the first detecting MOSFET applies the external voltage to drive the first adaptive bias circuit to turn on at least one of the six first stimulating MOSFETs disposed between the first central node and the first lower NMOSFET, so as to use the at least one of the six first stimulating MOSFETs and the second detecting MOSFET disposed between the first central node and the first lower NMOSFET to transmit a first physiological current from the physiological tissue to the signal detector.

5. The biomedical stimulation protection device according to claim 4, further comprising:
   a second upper PMOSFET electrically connected to the current source, wherein in the stimulation mode, the second upper PMOSFET receives the 4VDD and is turned off, so as to block the stimulation current from flowing the second upper PMOSFET;
   a second adaptive bias circuit configured to receive the VDD, 2VDD and 3VDD in the stimulation mode;
   a second lower NMOSFET electrically connected to ground, wherein the second lower NMOSFET receives the VDD and is turned on in the stimulation mode; and
   six second stimulating MOSFETs electrically cascoded with each other and electrically cascoded between the second upper PMOSFET and the second lower NMOSFET, and electrically connected to the second adaptive bias circuit, wherein a second central node among the six second stimulating MOSFETs comprises a second output terminal electrically connected to the physiological tissue, wherein in the stimulation mode, the second adaptive bias circuit turns on at least one of the six second stimulating MOSFETs disposed between the second central node and the second lower NMOSFET according to the VDD, 2VDD and 3VDD, so as to transmit the stimulation current from the physiological tissue to ground through the second lower NMOSFET, and form a second output voltage at the second output terminal;
   wherein according to the VDD, 2VDD, 3VDD and the second output voltage, the second adaptive bias circuit controls a voltage difference at two terminals of each of the second upper PMOSFET, the six second stimulating MOSFETs and the second lower NMOSFET to be lower than or equal to the VDD.

6. The biomedical stimulation protection device according to claim 5, wherein the VDD is 6 times of the threshold voltage of each of the second upper PMOSFET, the six second stimulating MOSFETs and the second lower NMOSFET.

7. The biomedical stimulation protection device according to claim 6, further comprising:
   a third detecting MOSFET electrically connected to the second adaptive bias circuit and the six second stimulating MOSFETs, wherein the third detecting MOSFET is turned off in the stimulation mode, and the third detecting MOSFET is turned on and receives the external voltage in the sampling mode; and
   a fourth detecting MOSFET electrically connected to the six second stimulating MOSFETs and the signal detector, wherein in the stimulation mode, the fourth detecting MOSFET is turned off, and in the sampling mode, the fourth detecting MOSFET is turned on, and the current source receives zero voltage and stops generating the stimulation current, the second upper PMOSFET receives the 4VDD and is turned off, the second adaptive bias circuit receives zero voltage, the second lower NMOSFET receives zero voltage and is turned off, the third detecting MOSFET applies the external voltage to drive the second adaptive bias circuit to turn on at least one of the six second stimulating MOSFETs disposed between the second central node and the second lower NMOSFET, so as to use the fourth detecting MOSFET and the at least one of the second stimulating MOSFETs disposed between the second central node and the second lower NMOSFET to transmit a second physiological current from the physiological tissue to the signal detector.

8. The biomedical stimulation protection device according to claim 7, wherein the first detecting MOSFET and the third detecting MOSFET are PMOSFETs, and the second detecting MOSFET and the fourth detecting MOSFET are NMOSFETs.

9. The biomedical stimulation protection device according to claim 7, wherein a gate of the first upper PMOSFET receives the 3VDD or zero voltage, a source of the first upper PMOSFET is electrically connected to the current source, and the six first stimulating MOSFETs comprise:
   a first PMOSFET comprising a source electrically connected to a drain of the first upper PMOSFET, and a gate receiving the 3VDD or zero voltage;
   a second PMOSFET comprising a source electrically connected to a drain of the first PMOSFET, and a gate electrically connected to the first adaptive bias circuit;
   a third PMOSFET comprising a source electrically connected to a drain of the second PMOSFET, a gate electrically connected to the first adaptive bias circuit, and a drain electrically connected to the first central node;
   a first NMOSFET comprising a drain electrically connected to the first central node, and a gate electrically connected to the gate of the third PMOSFET and the first adaptive bias circuit;
   a second NMOSFET comprising a drain electrically connected to a source of the first NMOSFET, and a gate electrically connected to the first adaptive bias circuit; and
   a third NMOSFET comprising a drain electrically connected to a source of the second NMOSFET, a gate receiving the VDD or zero voltage, and a source electrically connected to a drain of the first lower NMOSFET and the second detecting MOSFET, wherein the gate of the third NMOSFET is electrically connected to the first detecting MOSFET and the first adaptive bias circuit, the first lower NMOSFET comprises a gate receiving zero voltage and a source electrically connected to ground, wherein in the stimulation mode, the first adaptive bias circuit turns on the first PMOSFET, the second PMOSFET and the third PMOSFET according to the VDD, 2VDD and 3VDD, and the VDD is 6 times of a threshold voltage of each of the first PMOSFET, the second PMOSFET, the third PMOSFET, the first NMOSFET, the second NMOSFET and the third NMOSFET, wherein according to the VDD, 2VDD, 3VDD and the first output voltage, the first adaptive bias circuit controls a voltage difference at two terminals of each of the first PMOSFET, the second PMOSFET, the third PMOSFET, the first NMOSFET, the second NMOSFET and the third NMOSFET to be lower than or equal to the VDD, wherein in the sampling mode, the first detecting MOSFET applies the external voltage to drive the first adaptive bias circuit to turn on the first NMOSFET, the second NMOSFET and the third NMOSFET, so as to use the first NMOSFET, the second NMOSFET and the third NMOSFET to transmit the first physiological current to the signal detector.

10. The biomedical stimulation protection device according to claim 9, wherein the first adaptive bias circuit comprises:
    a fourth PMOSFET comprising a drain receiving the 2VDD or zero voltage;
    a fourth NMOSFET comprising a drain receiving the 2VDD or zero voltage, and a gate electrically connected to a gate of the fourth PMOSFET;
    a fifth NMOSFET comprising a drain receiving the 3VDD or zero voltage, wherein the drain and the gate of the fifth NMOSFET are electrically connected to the gate and the drain of the first PMOSFET, respectively, and a source of the fifth NMOSFET is electrically connected to the source of the fourth PMOSFET and the gate of the second PMOSFET;
    a sixth NMOSFET comprising a drain electrically connected to the source of the fifth NMOSFET, a gate electrically connected to the drain of the second PMOSFET, and a source electrically connected to the gates of the fourth PMOSFET, the third PMOSFET and the first NMOSFET;
    a fifth PMOSFET comprising a source electrically connected to the source of the sixth NMOSFET, a gate electrically connected to the source of the first NMOSFET, and a drain electrically connected to the source of the fourth NMOSFET and the gate of the second NMOSFET, and a base electrically connected to the source of the fifth PMOSFET, wherein the fifth PMOSFET comprises a first parasitic body-drain diode; and
    a sixth PMOSFET comprising a source electrically connected to the drain of the fifth PMOSFET, a gate electrically connected to the source of the second NMOSFET, a drain electrically connected to the first detecting MOSFET and the gate of the third NMOSFET, and a base electrically connected to the source of the sixth PMOSFET, wherein the sixth PMOSFET comprises a second parasitic body-drain diode, and the VDD is four to five times of a forward-biased voltage of each of the first parasitic body-drain diode and second parasitic body-drain diode, the drain of the sixth PMOSFET receives the VDD or zero voltage, wherein in the stimulation mode, the fourth PMOSFET, the fourth NMOSFET, the fifth NMOSFET, the sixth NMOSFET, the fifth PMOSFET and the sixth PMOSFET turn on the first PMOSFET, the second PMOSFET and the third PMOSFET according to the VDD, 2VDD and 3VDD, and the VDD is 6 times of a threshold voltage of each of the fourth PMOSFET, the fourth NMOSFET, the fifth NMOSFET, the sixth NMOSFET, the fifth PMOSFET and the sixth PMOSFET, wherein the VDD, 2VDD, 3VDD and the first output voltage are applied to the first PMOSFET, the second PMOSFET, the third PMOSFET, the first NMOSFET, the second NMOSFET and the third NMOSFET, to control a voltage difference at two terminals of each of the fourth PMOSFET, the fourth NMOSFET, the fifth NMOSFET, the sixth NMOSFET, the fifth PMOSFET and the sixth PMOSFET to be lower than or equal to the VDD, wherein in the sampling mode, the first detecting MOSFET applies the external voltage to drive the fifth PMOSFET and the sixth PMOSFET to turn on the first NMOSFET, the second NMOSFET and the third NMOSFET.

11. The biomedical stimulation protection device according to claim 10, wherein the gate of the second upper PMOSFET receives the 4VDD or zero voltage, the source of the second upper PMOSFET is electrically connected to the current source, and the six second stimulating MOSFETs comprise:
    a seventh PMOSFET comprising a source electrically connected to a drain of the second upper PMOSFET, and a gate receiving the 3VDD or zero voltage;
    an eighth PMOSFET comprising a source electrically connected to a drain of the seventh PMOSFET, and a gate electrically connected to the second adaptive bias circuit;
    a ninth PMOSFET comprising a source electrically connected to a drain of the eighth PMOSFET, a gate electrically connected to the second adaptive bias circuit, and a drain electrically connected to the second central node;
    a seventh NMOSFET comprising a drain electrically connected to the second central node, and a gate electrically connected to a gate of the ninth PMOSFET and the second adaptive bias circuit;
    an eighth NMOSFET comprising a drain electrically connected to a source of the seventh NMOSFET, and a gate electrically connected to the second adaptive bias circuit; and
    a ninth NMOSFET comprising a drain electrically connected to a source of the eighth NMOSFET, a gate receiving the VDD or zero voltage, a source electrically connected to the drain of the second lower NMOSFET and the fourth detecting MOSFET, wherein the gate of the ninth NMOSFET is electrically connected to the third detecting MOSFET and the second adaptive bias circuit, the gate of the second lower NMOSFET receives the VDD, a source of the second lower NMOSFET is electrically connected to ground, wherein in the stimulation mode, the second adaptive bias circuit turns on the seventh NMOSFET, the eighth NMOSFET and the ninth NMOSFET according to the VDD, 2VDD and 3VDD, and the VDD is 6 times of a threshold voltage of each of the seventh PMOSFET, the eighth PMOSFET, the ninth PMOSFET, the seventh NMOSFET, the eighth NMOSFET and the ninth NMOSFET, wherein according to the VDD, 2VDD, 3VDD and the second output voltage, the second adaptive bias circuit controls a voltage difference at two terminals of each of the seventh PMOSFET, the eighth PMOSFET, the ninth PMOSFET, the seventh NMOSFET, the eighth NMOSFET and the ninth NMOSFET to be lower than or equal to the VDD, and in the sampling mode, the third detecting MOSFET applies the external voltage to drive the second adaptive bias circuit to turn on the seventh NMOSFET, the eighth NMOSFET and the ninth NMOSFET, so as to use the seventh NMOSFET, the eighth NMOSFET and the ninth NMOSFET to transmit the second physiological current to the signal detector.

12. The biomedical stimulation protection device according to claim 11, wherein the second adaptive bias circuit comprises:
   a tenth PMOSFET comprising a drain receiving the 2VDD or zero voltage;
   a tenth NMOSFET comprising a drain receiving the 2VDD or zero voltage, and a gate electrically connected to a gate of the tenth PMOSFET;
   an eleventh NMOSFET comprising a drain receiving the 3VDD or zero voltage, wherein a drain and a gate of the eleventh NMOSFET are electrically connected to the gate and the drain of the seventh PMOSFET, respectively, and a source of the eleventh NMOSFET is electrically connected to a source of the tenth PMOSFET and the gate of the eighth PMOSFET;
   a twelfth NMOSFET comprising a drain electrically connected to the source of the eleventh NMOSFET, a gate electrically connected to the drain of the eighth PMOSFET, and a source electrically connected to the gates of the tenth PMOSFET, the ninth PMOSFET and the seventh NMOSFET;
   an eleventh PMOSFET comprising a source electrically connected to the source of the twelfth NMOSFET, a gate electrically connected to the source of the seventh NMOSFET, a drain electrically connected to a source of the tenth NMOSFET and the gate of the eighth NMOSFET, and a base electrically connected to the source of the eleventh PMOSFET, wherein the eleventh PMOSFET comprise a third parasitic body-drain diode; and
   a twelfth PMOSFET comprising a source electrically connected to the drain of the eleventh PMOSFET, a gate electrically connected to the source of the eighth NMOSFET, a drain electrically connected the third detecting MOSFET and the gate of the ninth NMOSFET, and a base electrically connected to the source of the twelfth PMOSFET, wherein the twelfth PMOSFET comprises a fourth parasitic body-drain diode, and the VDD is four to five times of a forward-biased voltage of each of the third parasitic body-drain diode and the fourth parasitic body-drain diode, the drain of the twelfth PMOSFET receives the VDD or zero voltage, wherein in the stimulation mode, the tenth PMOSFET, the tenth NMOSFET, the eleventh NMOSFET, the twelfth NMOSFET, the eleventh PMOSFET and the twelfth PMOSFET turn on the seventh NMOSFET, the eighth NMOSFET and the ninth NMOSFET according to the VDD, 2VDD and 3VDD, and the VDD is 6 times of a threshold voltage of each of the tenth PMOSFET, the tenth NMOSFET, the eleventh NMOSFET, the twelfth NMOSFET, the eleventh PMOSFET and the twelfth PMOSFET, wherein the VDD, 2VDD, 3VDD and the second output voltage are applied to the seventh PMOSFET, the eighth PMOSFET, the ninth PMOSFET, the seventh NMOSFET, the eighth NMOSFET and the ninth NMOSFET to control a voltage difference at two terminals of each of the tenth PMOSFET, the tenth NMOSFET, the eleventh NMOSFET, the twelfth NMOSFET, the eleventh PMOSFET and the twelfth PMOSFET to be lower than or equal to the VDD, wherein in the sampling mode, the third detecting MOSFET applies the external voltage to drive the eleventh PMOSFET and the twelfth PMOSFET to turn on the seventh NMOSFET, the eighth NMOSFET and the ninth NMOSFET.

* * * * *